US007922725B2

(12) United States Patent
Darst Rice et al.

(10) Patent No.: US 7,922,725 B2
(45) Date of Patent: Apr. 12, 2011

(54) METHOD AND ASSOCIATED INSTRUMENTATION FOR INSTALLATION OF SPINAL DYNAMIC STABILIZATION SYSTEM

(75) Inventors: Mark W. Darst Rice, Minneapolis, MN (US); Thomas J. Gisel, Chaska, MN (US); Hugh D. Hestad, Edina, MN (US); Mark J. Kroll, St. Paul, MN (US)

(73) Assignee: Zimmer Spine, Inc., Minneapolis, MN (US)

(*) Notice: Subject to any disclaimer, the term of this patent is extended or adjusted under 35 U.S.C. 154(b) by 1027 days.

(21) Appl. No.: 11/737,151

(22) Filed: Apr. 19, 2007

(65) Prior Publication Data

US 2008/0262551 A1 Oct. 23, 2008

(51) Int. Cl.
*A61B 17/70* (2006.01)

(52) U.S. Cl. ....... 606/86 A; 606/254; 606/259; 606/264; 606/270

(58) Field of Classification Search ........... 606/86 A, 606/99, 264–270, 254, 259
See application file for complete search history.

(56) References Cited

U.S. PATENT DOCUMENTS

| | | |
|---|---|---|
| 2,248,054 A | 7/1941 | Becker |
| 4,526,067 A | 7/1985 | Gaquere |
| 4,862,774 A | 9/1989 | Else et al. |
| 4,946,458 A | 8/1990 | Harms et al. |
| 5,030,220 A | 7/1991 | Howland |
| 5,261,913 A | 11/1993 | Marnay |
| 5,360,431 A | 11/1994 | Puno et al. |
| 5,458,030 A | 10/1995 | Betts |
| 5,540,688 A | 7/1996 | Navas |
| 5,562,660 A | 10/1996 | Grob |
| 5,584,831 A | 12/1996 | McKay |
| 5,672,176 A | 9/1997 | Biedermann et al. |
| 5,681,319 A | 10/1997 | Biedermann et al. |
| 5,989,254 A | 11/1999 | Katz |
| 6,112,623 A | 9/2000 | Bigand et al. |
| 6,139,549 A | 10/2000 | Keller |
| 6,183,472 B1 | 2/2001 | Lutz |
| 6,290,700 B1 | 9/2001 | Schmotzer |
| 6,402,752 B2 | 6/2002 | Schaffler-Wachter et al. |
| 6,471,705 B1 | 10/2002 | Biedermann et al. |
| 6,530,929 B1 | 3/2003 | Justis et al. |
| 6,695,843 B2 | 2/2004 | Biedermann et al. |
| 6,723,100 B2 | 4/2004 | Biedermann et al. |
| 6,736,820 B2 | 5/2004 | Biedermann et al. |
| 6,835,196 B2 | 12/2004 | Biedermann et al. |
| 6,896,677 B1 | 5/2005 | Lin |
| 6,905,500 B2 | 6/2005 | Jeon et al. |
| 6,918,911 B2 | 7/2005 | Biedermann et al. |
| 6,932,822 B2 | 8/2005 | Oribe et al. |

(Continued)

FOREIGN PATENT DOCUMENTS

EP 0669109 A1 8/1995

(Continued)

*Primary Examiner* — Eduardo C Robert
*Assistant Examiner* — Ellen C Hammond
(74) *Attorney, Agent, or Firm* — Seager, Tufte & Wickhem, LLC

(57) ABSTRACT

In one embodiment, a spinal stabilization apparatus includes a vertebral anchor having a head portion and a bone attachment portion. An elongate, flexible guide is removably coupled to the head portion of the vertebral anchor and has a channel extending longitudinally thereof and communicating with a slot in the head portion of the anchor. An elongate cord may be received within the channel to facilitate inserting and securing a spacer between pairs of anchors installed into adjacent vertebrae of a person's spine.

15 Claims, 6 Drawing Sheets

U.S. PATENT DOCUMENTS

| | | |
|---|---|---|
| 6,986,771 B2 | 1/2006 | Paul et al. |
| 6,989,011 B2 | 1/2006 | Paul et al. |
| 6,994,710 B2 | 2/2006 | White et al. |
| 7,008,424 B2 | 3/2006 | Teitelbaum |
| 7,018,378 B2 | 3/2006 | Biedermann et al. |
| 7,073,415 B2 | 7/2006 | Casutt et al. |
| 7,081,116 B1 | 7/2006 | Carly |
| 7,090,679 B2 | 8/2006 | Saint-Martin et al. |
| 7,250,052 B2 | 7/2007 | Landry et al. |
| 7,326,210 B2 | 2/2008 | Jahng et al. |
| 2001/0007074 A1 | 7/2001 | Strobel et al. |
| 2001/0012937 A1 | 8/2001 | Schaffler-Wachter et al. |
| 2002/0035366 A1 | 3/2002 | Walder et al. |
| 2002/0058942 A1 | 5/2002 | Biedermann et al. |
| 2002/0082602 A1 | 6/2002 | Biedermann et al. |
| 2002/0116001 A1 | 8/2002 | Schafer et al. |
| 2002/0133154 A1 | 9/2002 | Saint Martin |
| 2002/0133159 A1 | 9/2002 | Jackson |
| 2002/0138076 A1 | 9/2002 | Biedermann et al. |
| 2002/0143341 A1 | 10/2002 | Biedermann et al. |
| 2003/0018342 A1 | 1/2003 | Oribe et al. |
| 2003/0023243 A1 | 1/2003 | Biedermann et al. |
| 2003/0100896 A1 | 5/2003 | Biedermann et al. |
| 2003/0100904 A1 | 5/2003 | Biedermann |
| 2003/0114860 A1 | 6/2003 | Cavagna et al. |
| 2003/0125741 A1 | 7/2003 | Biedermann et al. |
| 2003/0187439 A1 | 10/2003 | Biedermann et al. |
| 2004/0097933 A1 | 5/2004 | Lourdel et al. |
| 2004/0102781 A1 | 5/2004 | Jeon |
| 2004/0122425 A1 | 6/2004 | Suzuki et al. |
| 2004/0138662 A1 | 7/2004 | Landry et al. |
| 2004/0143265 A1 | 7/2004 | Landry et al. |
| 2004/0153077 A1 | 8/2004 | Biedermann et al. |
| 2004/0176766 A1 | 9/2004 | Shluzas |
| 2004/0181224 A1 | 9/2004 | Biedermann et al. |
| 2004/0186474 A1 | 9/2004 | Matthis et al. |
| 2004/0225289 A1 | 11/2004 | Biedermann et al. |
| 2004/0243193 A1 | 12/2004 | Ballis |
| 2004/0249378 A1 | 12/2004 | Saint Martin et al. |
| 2005/0010220 A1 | 1/2005 | Casutt et al. |
| 2005/0055026 A1 | 3/2005 | Biedermann et al. |
| 2005/0065516 A1 | 3/2005 | Jahng |
| 2005/0065526 A1 | 3/2005 | Drew et al. |
| 2005/0085815 A1 | 4/2005 | Harms et al. |
| 2005/0124991 A1 | 6/2005 | Jahng |
| 2005/0131408 A1 | 6/2005 | Sicvol et al. |
| 2005/0131410 A1 | 6/2005 | Lin |
| 2005/0131421 A1 | 6/2005 | Anderson et al. |
| 2005/0143737 A1 | 6/2005 | Pafford et al. |
| 2005/0154389 A1 | 7/2005 | Selover et al. |
| 2005/0154390 A1 | 7/2005 | Biedermann et al. |
| 2005/0171542 A1 | 8/2005 | Biedermann et al. |
| 2005/0192579 A1 | 9/2005 | Jackson |
| 2005/0203513 A1 | 9/2005 | Jahng et al. |
| 2005/0234451 A1 | 10/2005 | Markworth |
| 2005/0267472 A1 | 12/2005 | Biedermann et al. |
| 2006/0084993 A1 | 4/2006 | Landry et al. |
| 2006/0084995 A1 | 4/2006 | Biedermann et al. |
| 2006/0106383 A1 | 5/2006 | Biedermann et al. |
| 2006/0111712 A1 | 5/2006 | Jackson |
| 2006/0111715 A1 | 5/2006 | Jackson |
| 2006/0142758 A1 | 6/2006 | Petit |
| 2006/0142761 A1 | 6/2006 | Landry |
| 2006/0155277 A1 | 7/2006 | Metz-Stavenhagen |
| 2006/0217738 A1 | 9/2006 | Tanimura |
| 2006/0230887 A1 | 10/2006 | Taguchi |
| 2007/0016200 A1 | 1/2007 | Jackson |
| 2007/0055244 A1 | 3/2007 | Jackson |
| 2007/0078461 A1 | 4/2007 | Shluzas |
| 2007/0129729 A1 | 6/2007 | Petit et al. |
| 2007/0198088 A1 | 8/2007 | Biedermann et al. |
| 2007/0270860 A1 | 11/2007 | Jackson |
| 2007/0293862 A1 | 12/2007 | Jackson |
| 2008/0091213 A1 | 4/2008 | Jackson |
| 2008/0140076 A1 | 6/2008 | Jackson |
| 2008/0147122 A1 | 6/2008 | Jackson |
| 2008/0177317 A1 | 7/2008 | Jackson |
| 2008/0183216 A1 | 7/2008 | Jackson |

FOREIGN PATENT DOCUMENTS

| | | |
|---|---|---|
| EP | 0669109 B1 | 8/1995 |
| EP | 0669109 B1 | 5/1999 |
| EP | 1523949 A1 | 4/2005 |
| EP | 1523949 B1 | 6/2007 |
| FR | 2715057 A1 | 7/1995 |
| FR | 2844180 A1 | 3/2004 |
| FR | 2867057 A1 | 9/2005 |
| NL | 7610576 | 3/1978 |
| WO | 8900028 | 1/1989 |
| WO | 9000377 | 1/1990 |
| WO | 9106254 | 5/1991 |
| WO | 9116020 | 10/1991 |
| WO | 9220294 | 11/1992 |
| WO | 9311715 | 6/1993 |
| WO | 9414384 | 7/1994 |
| WO | 9417745 A1 | 8/1994 |
| WO | 9501132 | 1/1995 |
| WO | 9513755 | 5/1995 |
| WO | 9513756 | 5/1995 |
| WO | 9514437 | 6/1995 |
| WO | 9519149 A1 | 7/1995 |
| WO | 9905980 A1 | 2/1999 |
| WO | 0027297 | 5/2000 |
| WO | 0101873 A1 | 1/2001 |
| WO | 02069854 A1 | 9/2002 |
| WO | 2004004549 A2 | 1/2004 |
| WO | 2004024011 A1 | 3/2004 |
| WO | 2004041100 A1 | 5/2004 |
| WO | 2005087121 A1 | 9/2005 |
| WO | 2006066685 A1 | 6/2006 |
| WO | 9812977 | 5/2007 |

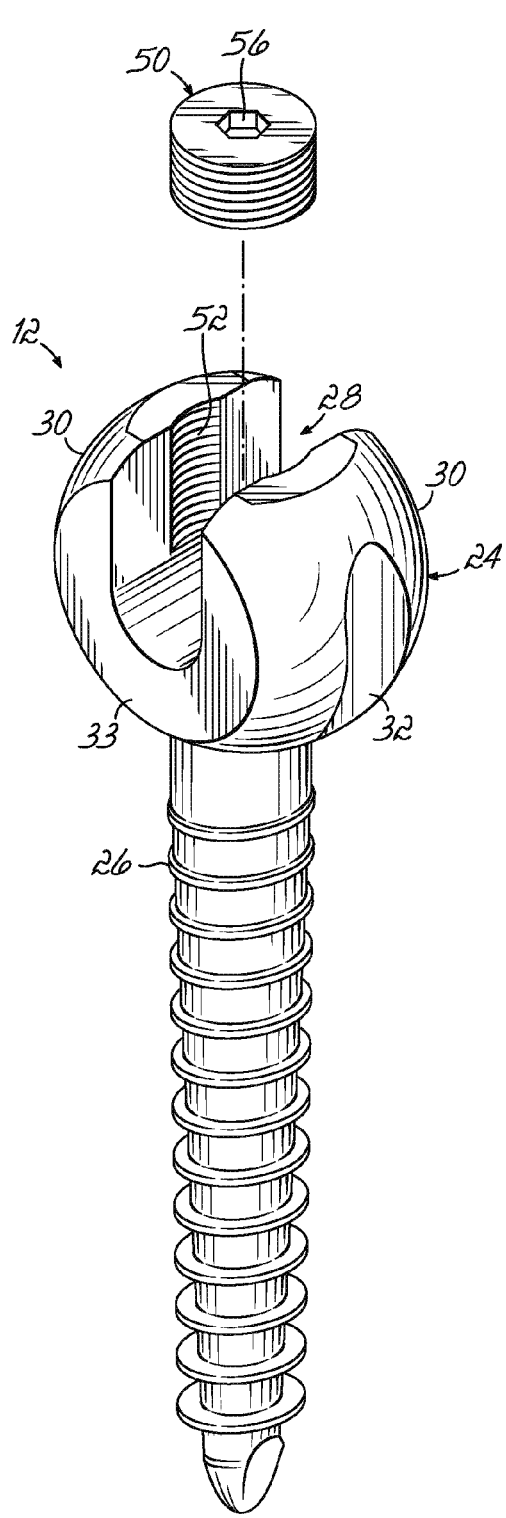
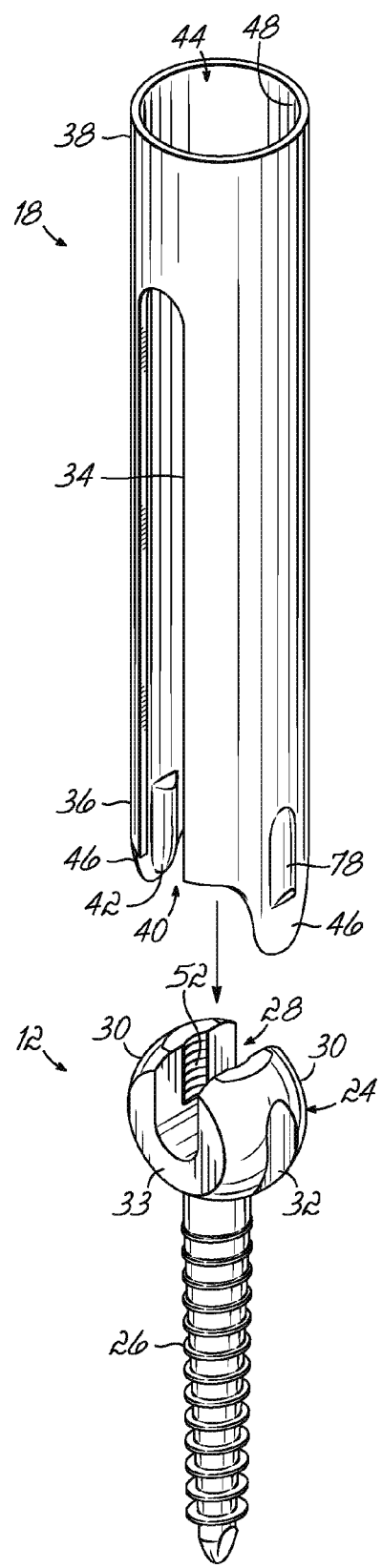
FIG. 1
FIG. 2

METHOD AND ASSOCIATED INSTRUMENTATION FOR INSTALLATION OF SPINAL DYNAMIC STABILIZATION SYSTEM

TECHNICAL FIELD

This invention relates generally to spinal support devices, and more particularly to methods and devices that facilitate installing an implantable system for providing dynamic stability of a person's spine.

BACKGROUND OF THE INVENTION

The treatment of acute and chronic spinal instabilities or deformities of the thoracic, lumbar, and sacral spine has traditionally involved the implantation of rigid rods to secure the vertebrae of a patient. More recently, flexible materials have been utilized in connection with securing elements, such as pedicle screws, to provide a dynamic stabilization of the spine. Such dynamic stabilization systems typically include a flexible spacer positioned between pedicle screws installed in adjacent vertebrae of person's spine. Once the spacer is positioned between the pedicle screws, a flexible cord is threaded through eyelets formed in the pedicle screws and an aperture through the spacer. The flexible cord retains the spacer between the pedicle screws while cooperating with the spacer to permit mobility of the spine. Traditional implantation of such dynamic stabilization systems may require relatively large surgical sites to permit threading the cord through the screws and spacer once the spacer has been positioned between the screws.

While some dynamic stabilization systems have been proposed for permitting the top loading of a spacer and cord between pedicle screws, these systems also require added instrumentation and procedures to distract the pedicle screws for placement of the spacer.

A need therefore exists for a spinal dynamic stabilization system and associated installation tools and techniques that overcome these and other drawbacks of the prior art.

SUMMARY OF THE INVENTION

This invention overcomes the foregoing and other shortcomings and drawbacks of spinal stabilization systems heretofore known for use in suitable various commercial and industrial environments. While various embodiments will be described herein, the invention is not limited to these embodiments. On the contrary, the invention includes all alternatives, modifications and equivalents as may be included within the spirit and scope of this invention.

In one embodiment, a system for stabilizing a patient's spine includes a pair of vertebral anchors adapted to be anchored to first and second vertebrae, respectively. Each vertebral anchor has an upwardly open channel. A connecting element that may be in the form of a flexible cord extends between the vertebral anchors and is seated in the channels. An annular spacer is positioned between the channels of the vertebral anchors with the connecting element passing there through. A pair of fasteners is each mated with the one of the channels of the vertebral anchors to secure the connecting element thereto. A pair of access members in the form of sleeves is mounted on the vertebral anchors and each sleeve has a cannula to provide percutaneous access to the vertebral anchor when mounted thereon.

A slot in each of the sleeves is in communication with the associated channel when mounted on the vertebral anchor. The system includes one tool having a tubular member with a cannula extending there through and configured to fit over one of the sleeves when mounted on the associated vertebral anchor. The tool is used by the surgeon to advance the connecting member along the slot and into the channel of one of the vertebral anchors and to position the spacer between the vertebral anchors. In alternative embodiments, the tool may have an arcuate flange on its distal end to cradle the spacer for distraction during insertion between the vertebral anchors.

The system may include another tool also having a tubular member with a cannula extending there through and configured to fit over one of the sleeves when mounted on the associated vertebral anchor. This tool is adapted to advance the connecting member along the slot and into the channel of the vertebral anchors. This tool may include a mating feature proximate the distal end and complementary to a mating feature on either the vertebral anchor or the sleeve to thereby couple the tool thereto. The complementary mating features may include a recess on the distal end of the tool, a recess on the head of the pedicle screw, an outwardly directed protrusion proximate a distal end of the sleeve, and an inwardly directed protrusion proximate the distal end of the sleeve. The recesses are configured to mate with the protrusions to releasably secure the tool to the pedicle screw and allow the surgeon to use the tool to screw the pedicle screws into the vertebrae.

Other embodiments of this invention involve the installation procedures for a spinal stabilization construct and include installing the vertebral anchors onto the vertebrae and mounting access members, which in one embodiment are sleeves, onto the vertebral anchors. Each sleeve has a cannula to provide percutaneous access to the channel of the respective vertebral anchor. The connecting element is inserted through a slot in one of the sleeves and is advanced from the slot into the channel in the associated vertebral anchor. The connecting element is secured to the channel of the vertebral anchor with a fastener and an annular spacer is positioned on the connecting element adjacent the vertebral anchor.

The connecting element is inserted through a slot in the other sleeve and advanced into the channel in the second vertebral anchor. The spacer distracts against the first vertebral anchor and positions the spacer between the vertebral anchors. The connecting element is secured to the channel of the second vertebral anchor with a second fastener. The connecting element may be a flexible cord that is tensioned between the vertebral anchors. The respective fasteners may be passed through the sleeves percutaneously to the respective channels in conjunction with the tensioning of the cord or connecting element.

These and other features, objects and advantages of the invention will become more readily apparent to those skilled in the art in view of the following detailed description, taken in conjunction with the accompanying drawings.

BRIEF DESCRIPTION OF THE DRAWINGS

The accompanying drawings, which are incorporated in and constitute a part of this specification, illustrate embodiments of the invention and, together with the general description of the invention given above, and the detailed description given below, serve to explain the principles of the invention.

FIG. 1 is a perspective view of a vertebral anchor in the form of a pedicle screw and an associated fastener in the form of a set screw according to one aspect of this invention;

FIG. 2 is a perspective view of the vertebral anchor of FIG. 1 being coupled to an access sleeve according to one aspect of this invention;

DETAILED DESCRIPTION

Figure 3:
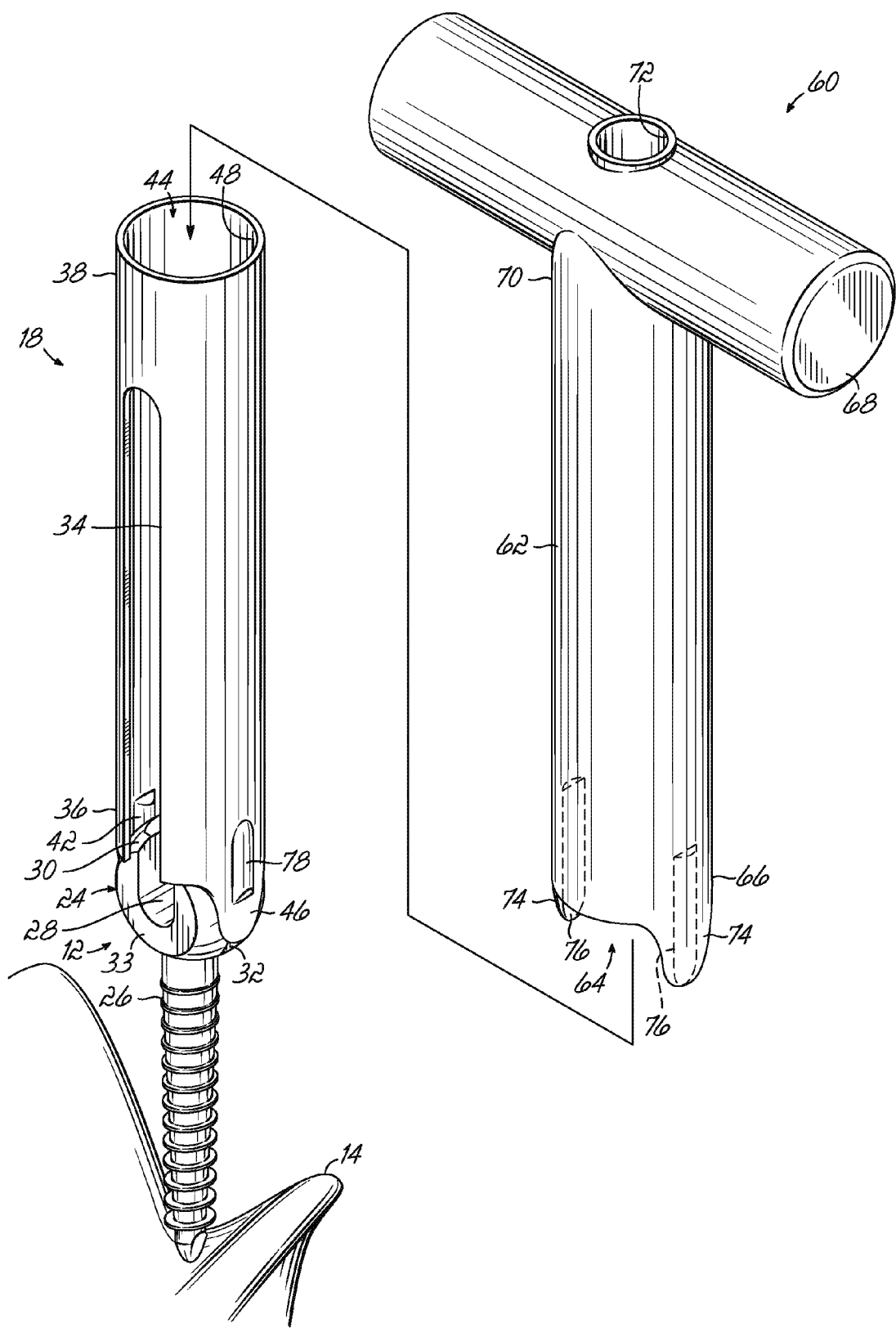
FIG. 3 is a perspective view of the components of FIG. 2 being coupled to a tool according to another aspect of this invention.

FIGS. 1-2 and 6-7 depict some of the components of one embodiment of a spinal stabilization system 10 according to this invention. Specifically, vertebral anchors 12 are adapted to be installed into adjacent vertebrae 14, 16 of the spine using removable access members 18 inserted through an incision formed through the patient's skin. The incision may be sized for minimally invasive percutaneous or retractor based techniques or may be used in open procedures. In the embodiment shown, at least two anchors 12, shown here in the form of pedicle screws, are fixedly installed into the pedicle area of adjacent vertebrae 14, 16 and a flexible spacer 20 is disposed there between to control motion of the spine, while otherwise leaving the spinal segment mobile. Alternatively, the two anchors can be placed in a patient in combination with a fusion device located between the vertebral bodies.

The spacer 20 and pedicle screws 12 are coupled together by a connecting element 22 which in one embodiment is a flexible member coupled to or passed through the spacer 20 and secured to the heads 24 of the screws 12. Such spacers 20 and flexible members 22 may be similar to those used in the Dynesys® Dynamic Stabilization System available from Zimmer Spine of Minneapolis, Minn. In one embodiment, the spacer 20 may be formed from polycarbonate urethane and the flexible member 22 is a cord that may be formed from polyethylene-terephthalate, although it will be recognized that various other materials suitable for implantation within the human body and for providing stabilization of the spine while maintaining flexibility may be used.

In one embodiment, the anchor 12 is a pedicle screw having a threaded shank 26 configured to be screwed into the pedicle area of a vertebra 14, 16. The head 24 of the screw is configured to receive and secure the flexible member 22. In the embodiment shown, the head 24 includes an upwardly open channel 28 formed between upwardly directed arms 30 and extending generally transverse to the longitudinal axis of the shank 26 and having an open end opposite the shank 26 for receiving the flexible member 22 into the channel 28 of the head 24 in a top loading fashion. Accordingly, the channel 28 alleviates the need to thread the flexible member 22 through an eyelet of the head 24 of the anchor 12 after the anchor 12 has been installed into the vertebral body 14, 16 of a patient's spine. The head 24 may have a pair of spaced, generally flat face 33 for juxtaposition to the spacer 20.

In this embodiment, the head 24 of the pedicle screw 12 has receiving channels, such as recesses 32, provided on oppositely disposed sides of the arms 30 of the head 24 to facilitate screwing the anchor 12 into a vertebra 14, 16 of a patient's spine using a tool as described later herein. In one embodiment, the pedicle screw 12 is formed from a titanium alloy, but it will be recognized that various other materials suitable for implantation within the human body and having sufficient strength to be securely attached to the bone and to secure the flexible member 22 may be used. While a uniaxial pedicle screw is shown and described herein, it will be recognized that the anchor 12 may alternatively comprise a hook, a polyaxial pedicle screw, or various other structure suitable to be secured to a vertebral body.

An elongate access member 18 is removably secured to the head 24 of the pedicle screw 12 and is formed substantially from a resilient, flexible material that permits deformation or bending of the access member 18 along its length without transmitting significant force to the pedicle screw 12. For example, the access member 18 may be formed from polymeric material such as nylon, polyethylene, polyurethane, or various other polymeric materials that are biocompatible and provide sufficient flexibility to permit the guides to bend in flexure along their length without transmitting significant force to the pedicle screw 12. In other exemplary embodiments, the access members 18 may be configured as a rigid or a composite structure, comprising a portion formed from a substantially rigid material and a portion comprising a flexible material or wholly of a rigid material.

In the embodiment shown in FIG. 2, the access member 18 includes a pair of diametrically opposed, longitudinal slots 34 extending from a first, distal end 36 toward a second, proximal end 38 of the access member 18. Each slot 34 has an opening 40 at the first end 36 that is shaped to mate with the head 24 of the pedicle screw 12 such that the slot 34 communicates with the channel 28 formed in the head 24 of the pedicle screw 12. In this arrangement, the longitudinally extending slot 34 may be used to guide the flexible member 22 from the slots 34 of the access member 18, along its length, and into the channel 28 formed in the head 24 of the pedicle screw 12.

In one embodiment, the access member 18 includes mating tabs 42 to mate with the receiving channels or recesses 32 on the head 24 of the pedicle screw 12. In the exemplary embodiment shown, the mating tabs 42 are inwardly direct protrusions. Mating surfaces between the pedicle screw and the access member 18 are configured to provide a mechanical interlock that is sufficient to withstand forces applied to the access member 18 during installation of the pedicle screws 12 into the vertebrae 14, 16 and installation of the spacer 20 between adjacent pedicle screws 12. However, the access members 18 may be removed from the heads 24 of the pedicle screws 12, for example, by application of an appropriate force or by manipulating the access member 18 relative to the pedicle screw 12, to cause the mating tabs 42 on the access member 18 to dislodge from the recesses 32 on the head 24 of the pedicle screw 12. The access member 18 may be formed in a molding process in the form of a sleeve having a longitudinally extending cannula 44, and may thereafter be joined to the head 24 of the pedicle screw 12 by mechanically interlocking the sleeve 18 onto the head 24 the pedicle screw 12 with the mating tabs 42 and receiving channels like recesses 32.

With continued reference to FIGS. 1-2, the sleeve 18 includes an aperture 48 proximate the second end 38 for receiving various components including a fastener 50, such as a set screw, for securing the flexible member 22 to the head 24 of the pedicle screw 12, as will be described more fully below. The aperture 48 leads to the cannula 44 of the access member 18 to provide percutaneous access to the head 24 of the pedicle screw 12.

Longitudinally extending and laterally oriented threads 52 are formed on the inwardly facing surfaces of the arms 30 in the channel 28 of the head 24. The threads 52 are sized for engagement with the fastener 50 when it is desired to secure the flexible member 22 to the head 24 of the pedicle screw 12. In one embodiment, a driver 54 (FIG. 7) or other tool suitable for engaging a socket 56 in a top face of the fastener, or set screw, 50 may be inserted through the cannula 44.

While the fastener 50 has been shown and described herein as comprising a set screw, it will be recognized that various other types of securing members may alternatively be used to secure the flexible member 22 to the head 24 of the anchor 12. Likewise, the sleeve 18 may be configured to accommodate these various other types of fasteners and to percutaneously provide access for them to the anchor 12.

Figure 4:
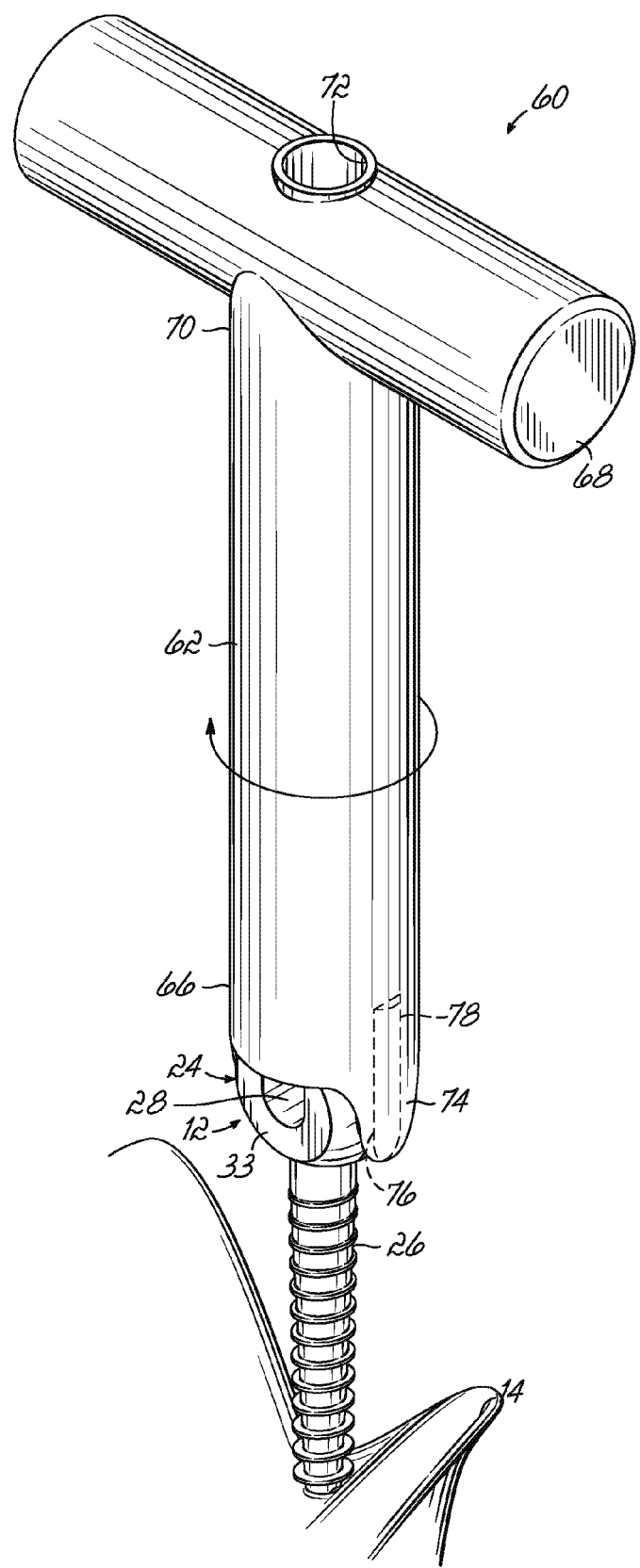
FIG. 4 is a perspective view of the components of FIG. 3 being used to screw a first vertebral anchor into a vertebrae of a patient.

Referring now to FIG. 3, use of a tool 60 to install components of the spinal stabilization system 10 to the vertebrae 14, 16 of a spine will now be described. Vertebral anchor 12 and sleeve 18 mated together have been inserted through a minimally invasive incision formed in a patient's skin to be threadably secured into the pedicle areas of a vertebrae 14, 16. The tool 60 in one embodiment as shown includes a tubular member 62 extending longitudinally and defines a central cannula 64 extending from a distal end 66 of the tool 60. The tool 60 includes a handle 68 at the proximal end 70 of the tubular member 62 and the handle 68 and tubular member 62 in combination form a generally T-shaped configuration according to one embodiment of the tool 60. In one embodiment, the T-shaped handle configuration of handle 68 can be incorporated into the sleeve 18. The proximal end 70 of the cannula 64 in the tubular member 62 is accessed through a port 72 in the handle 68 as shown in FIGS. 3 and 4. The port 72 is sized to receive a fastener 50. The handle 68 provides a convenient grip for a surgeon to grasp the tool 60 for manipulation during installation of the spinal stabilization system 10. The distal end 66 of the tubular member 62 includes a pair of diametrically opposed fingers 74 projecting downwardly. Tool receiving channels, such as recesses 76, are formed on an inner face of each finger 74 and extends longitudinally toward the body portion of the tubular member 62. The cannula 64 and tubular member 62 are sized and configured to fit over the access member 18 and pedicle screw 12 combination as shown in FIG. 3.

Referring to FIG. 4, with the tool 60 installed onto and over the access member 18 and pedicle screw 12 in a generally telescopic arrangement, the recesses 76 at the distal end 66 of the tubular member 62 mate with outwardly directed tool mating tabs 78 on the distal end of the access member 18. As a result, the tool 60 is mated with the vertebral anchor 12 and access member 18. The mating interaction of the mating tabs 42, 78 and recesses 32, 76 allow the T-shaped tool 60 to drive the pedicle screw 12 as well as act as an anti-torque instrument. The surgeon rotates the tool 60 mated with the vertebral anchor 12 and access member 18 to screw the vertebral anchor 12 into the vertebrae 14, 16. The tool 60 can then be uncoupled from the access member 18 by dislodging the tool mating tabs 78 from the recess 76, thereby leaving the access member 18 mounted on the pedicle screw 12 installed on the vertebrae 14, 16.

Figure 5:
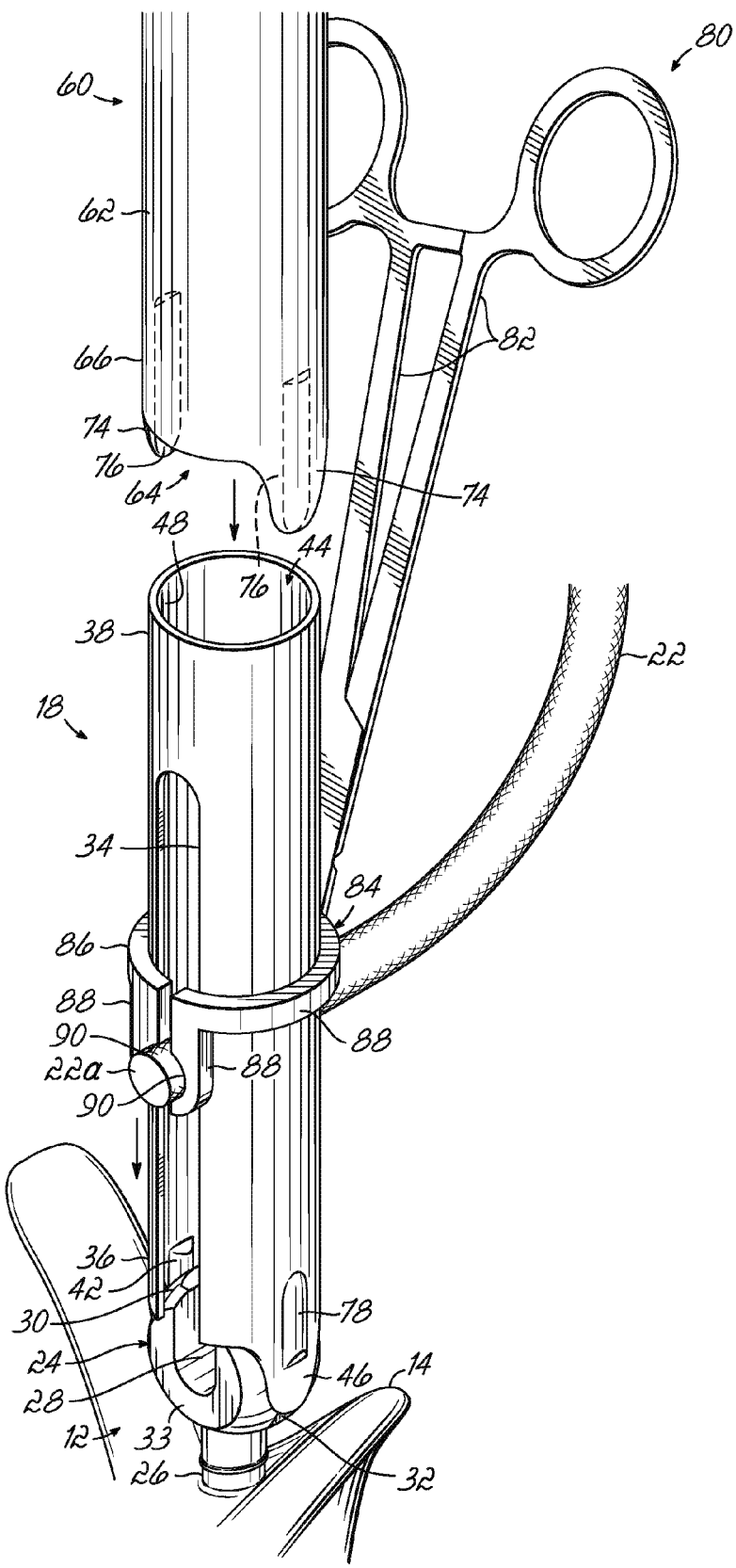
FIG. 5 is a perspective view of a connecting element of a dynamic stabilization system being installed on the first vertebral anchor of FIG. 4.

The above-described description of the installation of the pedicle screw 12 may be performed on each of the pedicle screws 12 utilized in the stabilization system 10 as appropriate. In FIG. 5, the attachment of the connecting member, such as the exemplary flexible member 22 in the form of a flexible cord, to one of the pedicle screws 12 is shown. The pedicle screw 12 installed in the vertebrae 14 has the access member 18 mounted thereto as shown in FIG. 5. A terminal end 22a of the connecting element 22 is inserted through the slots 34 of the access member 18 and this is likely performed at a portion of the slots 34 and access member 18 extending from the patient's body and above the incision. A forceps 80 having a pair of elongate handle members 82 pivotally coupled together can be utilized to stabilize and maneuver the flexible member 22 in the access member slots 34. The forceps 80 include cooperating jaws 84, each of which has an arcuate portion 86 and a downwardly depending leg 88 with a notch go proximate the distal end of the leg 88 as shown in FIG. 5. In combination, the jaws 84 of the forceps 80 surround the access member 18 and the notches go clamp the end 22a of the flexible member 22 projecting through the slot 34. Any excess portion of the flexible member 22 that overhangs the notches go may be severed or trimmed as desired.

With the flexible member 22 clamped by the forceps 80 and projecting through the slots 34 in the access member 18 as shown in FIG. 5, the flexible member 22 may be passed through the slots 34 and down to the channel 28 of the pedicle screw 12. The forceps 80 clamped onto the flexible member 22 and around the access member 18 may be utilized to push the flexible member 22 from the slots 34 and into the channel 28. Alternatively, the tubular member 62 of the tool 60 may be used in combination with the forceps 80 to advance the flexible member 22 from the slots 34 downwardly and into the upwardly open channel 28 of the pedicle screw 12 as shown in FIG. 5.

With the flexible member 22 seated in the channel 28 and secured therein by the forceps 80, the fastener or set screw 50 may be percutaneously introduced through the cannula 44 of the access member 18 for securing the flexible member 22 to the pedicle screw 12. A driver 54 or similar tool may be utilized to threadably secure the set screw 50 to the head 24 of the pedicle screw 12 thereby securing the flexible member 22 to the pedicle screw 12. The tubular member 62 and T-shaped tool 60 may continue to be mounted telescopically on the access member 18 and pedicle screw 12 or removed for easier access and installation of the set screw 50.

Figure 6:
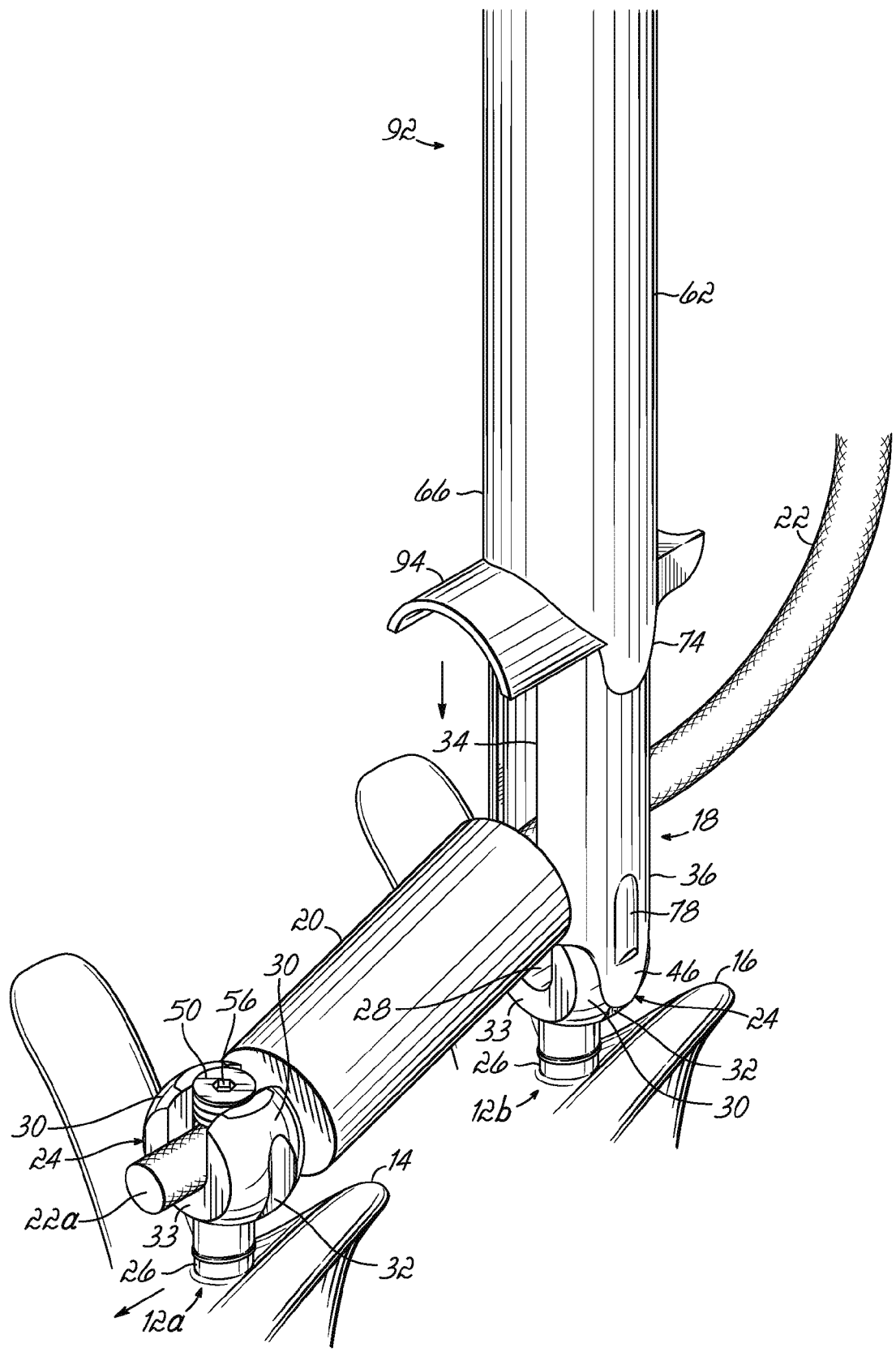
FIG. 6 is a perspective view of the components of the dynamic stabilization system being installed relative to a pair of vertebral anchors installed on respective vertebrae of the patient.
Figure 7:
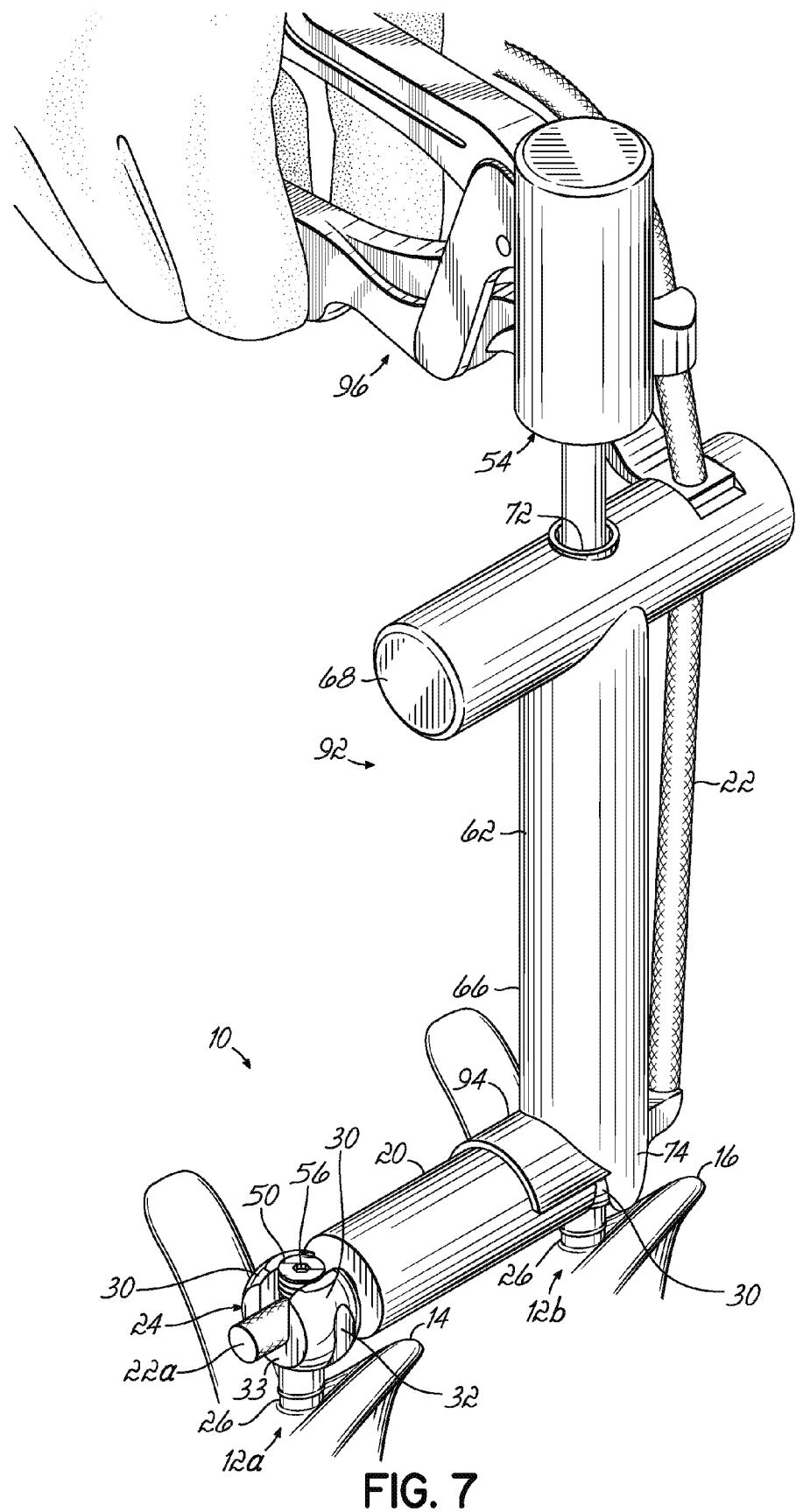
FIG. 7 is a perspective view of the connecting element of the dynamic stabilization system being tensioned between the vertebral anchors and the anchors being distracted during the tensioning process.

Referring to FIGS. 6 and 7, the adjacent pedicle screw 12a has been placed in the associated vertebrae 14 with the procedure as previously described. The spacer 20 is then put over the flexible member 22 and slid into contact with the head 24 of the first pedicle screw 12a as shown in FIG. 6. The tool 62 can be used to create distraction between the vertebral anchors 12a, 12b to allow for easier placement of the spacer 20 between the vertebral anchors 12a, 12b. Alternatively, a distractive force can be generated by the placement of the spacer 20 between the vertebral anchors 12a, 12b. As the tool 62 shown in FIG. 6 is forced into engagement with the spacer 20, the spacer 20 then generates a force against the vertebral anchors 12a, 12b thus creating distraction of the vertebrae.

The flexible member 22 is then inserted through the slots 34 of the access member 18 on the second pedicle screw 12b and a connecting element guide tool 92 can be slid over the access member 18 on the second pedicle screw 12b as shown in FIGS. 6 and 7. The cord guide tool 92 is similar to the T-shaped tool 60 previously described in FIGS. 3 and 4 with like reference numerals identifying similar features. The flexible member guide tool 92 also includes at least one arcuate flange 94 projecting generally perpendicularly from the axis of the tubular member 62. The arcuate flange 94 is sized and configured to cradle a portion of the spacer 20 as the tool 92 is pushed downwardly over the access member 18. The arcuate flange 94 contacts the end of the spacer 20 adjacent the second pedicle screw 12b and downward pressure on the tool 92 forces the spacer 20 downwardly and into position between the adjacent pedicle screw heads 24. As the cord guide tool 92 slides downwardly over the access member 18, the arcuate flange 94 translates the spacer 20 downward and outward to create distraction by reacting to the force of the flexible member guide tool 92 and pushing against the access member 18 on the second pedicle screw 12*b* and the head 24 of the first pedicle screw 12*a*. Simultaneously, the flexible member 22 advances from the slots 34 of the access member 18 on the second pedicle screw 12*b* and into the channel 28 of the head 24 of the second pedicle screw 12*b*.

Advantageously, this invention utilizes the tools and spacer to create distraction between the pedicle screw heads 24 and avoids threading the flexible member 22 through an eyelet in the head of the pedicle screw and any over distraction caused by the thickness of the flexible member when pulled into position.

Once the spacer 20 is positioned between the pedicle screw heads 24 and the flexible member 22 is seated in the channel 28 of the second pedicle screw 12*b*, the flexible member 22 may be tensioned utilizing a tensioning tool 96 as shown in FIG. 7. After the flexible member 22 is appropriately tensioned, the set screw 50 may be passed through the port 70 in the handle 68 of the cord guide tool 92 and seated in the channel 28 of the pedicle screw head 24. The driver 54 is then utilized through the cannula 64 of the tool 92 and the access member 18 to mate with the set screw 50 and rotate the set screw 50 into secure engagement in the channel 28 and thereby clamp the tensioned flexible member 22. The driver 54, cord guide tool 92, access member 18 and tensioning tool 96 may then be removed from the patient and the flexible member 22 trimmed to length. Alternatively, if a multi-level spinal dynamic stabilization system 10 is to be installed, the process is repeated on subsequent vertebrae as appropriate and the incision closed to complete the installation.

While this invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept

What is claimed is:

1. A system for stabilizing a patient's spine comprising:
   first and second vertebral anchors adapted to be anchored to first and second vertebrae, respectively, each vertebral anchor having an upwardly open channel;
   a flexible connecting element adapted to extend between the vertebral anchors and be seated in the channels;
   a spacer adapted to be positioned between the channels of the vertebral anchors with the connecting element passing there through;
   first and second fasteners adapted to be mated with the channels of the first and second vertebral anchors, respectively, to secure the flexible connecting element thereto;
   first and second access members adapted to be mounted on the first and second vertebral anchors, respectively, each access member having an opening to provide access to the vertebral anchor when mounted thereon;
   a slot in each of the access members in communication with the associated channel when mounted on the vertebral anchor; and
   a first tool slidably engagable with and configured to translate along an exterior of the first access member without rotation when the first access member is mounted on the associated vertebral anchor to advance the flexible connecting member along the slot and into the channel of one of the vertebral anchors and to position the spacer between the vertebral anchors.

2. The system of claim 1 wherein the flexible connecting element is a flexible cord adapted to be tensioned between the vertebral anchors.

3. The system of claim 1 wherein each fastener is a set screw adapted to be threadably mated with the vertebral anchor.

4. The system of claim 1 further comprising:
   a handle on the proximal end of the first tool adapted to be grasped by a surgeon for manipulation of the first tool.

5. The system of claim 1 further comprising:
   a second tool having a tubular member with a cannula extending there through and configured to fit over one of the access members when mounted on the associated vertebral anchor, the second tool being adapted to advance the flexible connecting member along the slot and into the channel of one of the vertebral anchors.

6. The system of claim 5 further comprising:
   a handle on the proximal end of the second tool adapted to be grasped by a surgeon for manipulation of the second tool.

7. The system of claim 6 further comprising:
   complementary mating features proximate the distal end of the second tool and at least one of the vertebral anchors and the access members to thereby couple the second tool thereto.

8. The system of claim 7 wherein each vertebral anchor is a pedicle screw having a threaded shaft and a head, the channel being formed in the head, the second tool being adapted to screw the threaded shaft into the vertebrae upon rotation of the second tool when mated with the pedicle screw.

9. The system of claim 8 wherein the complementary mating features further comprise:
   a first recess on the distal end of the second tool;
   a second recess on the head of the pedicle screw;
   a first, outwardly directed, protrusion proximate a distal end of the access member; and
   a second, inwardly directed, protrusion proximate the distal end of the access member;
   wherein the first and second recesses are configured to mate with the first and second protrusions, respectively.

10. The system of claim 1 wherein each access member further comprises:
    a sleeve with a pair of longitudinal diametrically opposed slots.

11. A system for stabilizing a patient's spine comprising:
    first and second pedicle screws each having a threaded shaft and a head with an upwardly open channel, the first and second pedicle screws adapted to be anchored to first and second vertebrae, respectively;
    a flexible member adapted to extend between the pedicle screws and be seated in the channels;
    a spacer adapted to be positioned between the heads of the pedicle screws with the flexible member passing there through;
    first and second set screws adapted to be mated with the channels of the first and second pedicle screws, respectively, to secure the flexible member thereto;
    first and second sleeves adapted to be mounted on the first and second pedicle screws, respectively, each sleeve having a cannula to provide access to the pedicle screw when mounted thereon;

a longitudinal slot in each of the sleeves in communication with the associated channel when mounted on the pedicle screw;

a first tool having a tubular member with a cannula extending there through and configured to fit over one of the sleeves when mounted on the associated pedicle screw, the first tool being adapted to advance the flexible member along the slot and into the channel of one of the pedicle screws and to position the spacer between the pedicle screws;

a second tool having a tubular member with a cannula extending there through and configured to fit over one of the sleeves when mounted on the associated pedicle screw, the second tool being adapted to advance the flexible member along the slot and into the channel of one of the pedicle screws; and complementary mating features proximate the distal end of the second tool and at least one of the pedicle screws and the sleeves to thereby couple the second tool thereto, the second tool being adapted to screw the threaded shaft into the vertebrae upon rotation of the second tool when mated with the pedicle screw.

12. The system of claim 11 further comprising:

an arcuate flange on a distal end of the first tool adapted to cradle the spacer for distraction between the vertebral anchors.

13. The system of claim 11 wherein the complementary mating features further comprise:

a first recess on the distal end of the second tool;

a second recess on the head of the pedicle screw;

a first, outwardly directed, protrusion proximate a distal end of the sleeve; and a second, inwardly directed, protrusion proximate the distal end of the sleeve;

wherein the first and second recesses are configured to mate with the first and second protrusions, respectively.

14. A system for stabilizing a patient's spine comprising:

first and second vertebral anchors adapted to be anchored to first and second vertebrae, respectively, each vertebral anchor having an upwardly open channel;

a flexible connecting element adapted to extend between the vertebral anchors and be seated in the channels;

a spacer adapted to be positioned between the channels of the vertebral anchors with the connecting element passing there through;

first and second fasteners adapted to be mated with the channels of the first and second vertebral anchors, respectively, to secure the flexible connecting element thereto;

first and second access members adapted to be mounted on the first and second vertebral anchors, respectively, each access member having an opening to provide access for the passage of one of the fasteners to the respective vertebral anchor when mounted thereon;

a slot in each of the access members in communication with the associated channel when mounted on the vertebral anchor; and a first tool having an elongate shaft and a flange at a distal end of the elongate shaft projecting generally perpendicularly from an axis of the elongate shaft and having a lower arcuate surface shaped to cradle the spacer for distraction between the vertebral anchors, the first tool configured to be slidably engaged with and translated along an exterior of the first access member when mounted the first access member is on the associated vertebral anchor to position the spacer between the vertebral anchors.

15. The system of claim 14 wherein the first tool is configured to translate along the exterior of the first access member without rotation to position the spacer between the vertebral anchors.

* * * * *